March 3, 1964 W. E. LAMMERTS Plant Pat. 2,369
ROSE PLANT
Filed Feb. 11, 1963
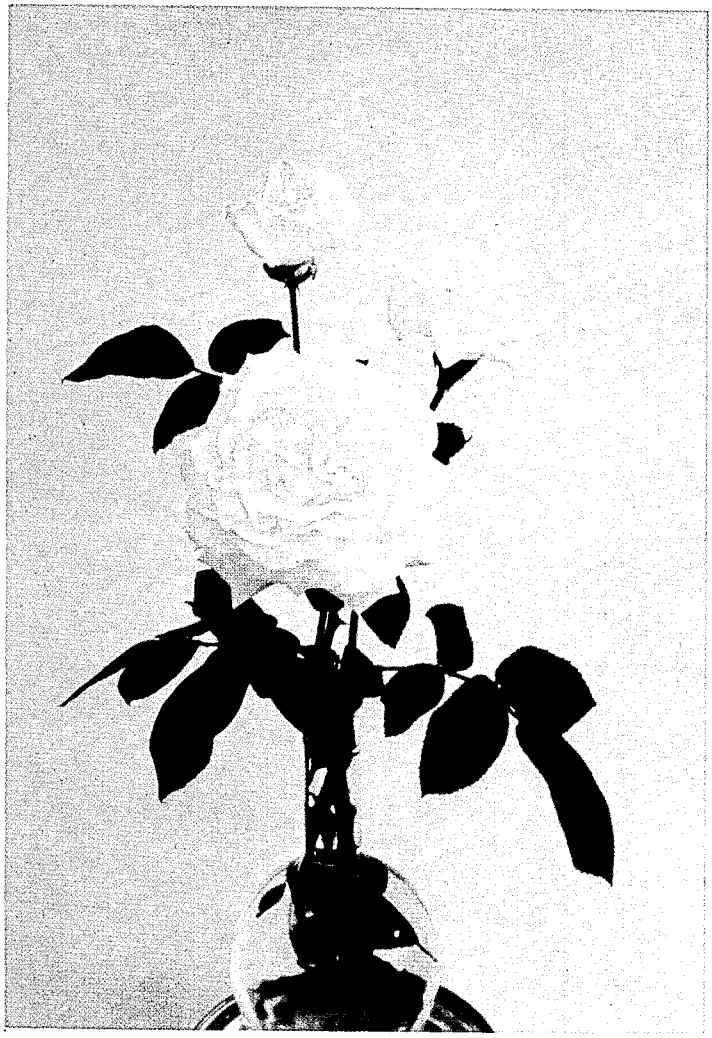
INVENTOR:
WALTER E. LAMMERTS
BY Rummler + Lucow
ATT'YS United States Patent Office Plant Pat. 2,369
Patented Mar. 3, 1964

2,369
ROSE PLANT

Walter E. Lammerts, Livermore, Calif., assignor to Amling-Devor Nurseries, Inc., Livermore, Calif., a corporation of California Filed Feb. 11, 1963, Ser. No. 257,803
1 Claim. (Cl. Plt.—18)

This disclosure concerns a new and distinct variety of hybrid tea rose plant developed by me through breeding efforts carried on at Livermore, California since 1956.

My new rose plant variety originated as a selected seedling created by a cross between "Queen Elizabeth" (Plant Patent 1,259) as the seed parent and "Fashion" (Plant Patent 789) as the pollen parent. I have reproduced this new variety asexually, by budding, at Livermore, California and further propagation of the new variety, by budding, has demonstrated that its new and distinctive characteristics are fixed and hold true to form.

The objective sought by my aforesaid breeding efforts was to create a rose having the color of "Fashion" combined with good hot house qualities such as (1) high production, (2) sufficient substance for good keeping quality during shipping as well as in vase work, (3) a high centered imbricate flower arrangement, and (4) enough petals to be long lasting. This objective has been substantially accomplished and the resulting new variety is a specialty type medium-sized rose of very dainty and unusual color and having exquisitely arranged petals, the bloom being high centered and opening in a regularly imbricate manner. The new variety most nearly resembles "Fashion," its pollen parent, in color and "Picture" (unpatented) in flower size.

My new variety of rose plant is shown in the accompanying full color illustration which shows buds as well as a fully opened bloom and the nature of the foliage.

The following is a description, in detail, of my new rose plant variety, the color designations set forth being according to the Horticultural Color Chart of the British Colour Council.

*The Plant*

Origin: Seedling.
Parentage:
*Seed parent.*—Queen Elizabeth (P.P. 1259).
*Pollen parent.*—Fashion (P.P. 789).
Classification:
*Botanic.*—Hybrid tea.
*Commercial.*—Hot house use.
Form: Low, bushy, outdoors.
Heighth: 3 to 3½ feet, when grown outdoors.
Growth: Moderate and sturdy, but not coarse, upright and in the greenhouse its vigor is comparable to Better Times (P.P. 23).
Branching: Upright and compact in habit. Branches profusely and at least two from each cutback.
Strength: Medium vigor.
Foliage:
*Quantity.*—Abundant, with each leaf having 5 or 7 medium large leaflets.
*Size of leaf.*—3½ to 3¾ x 4½ to 5 inches.
*Shape of leaflet.*—Elliptic, terminating gradually in a ¼ to ½ inch point, and having small, regular serrations.
*Texture.*—Soft, smooth and of dull appearance.
*Color.*—Upper side—Spinach Green (0960/1). Under side—Sage Green (000861/1).
*Petioles.*—Length—1⅛ to 1¼ inches.
*Ribs and veins.*—Not strongly indented on upper surface, and rather prominently obtruding on under side of leaflets.

*Rachis.*—Usually with 2, sometimes 3, small thorns.
Plant has thorns and prickles:
*Color of thorns.*—Yellow Ochre (07/3) at base, tinged with Light Garnet Brown (00918/3).
*Size of thorns.*—Usually ⅛ inch wide by ¼ to ⅜ inch long as base. Usually up to ⅜ inch high and slightly recurved.

*Bud*

Size: Medium large—1⅛ to 1¼ inches in diameter. 1½ to 1⅝ inches in depth.
Form: Very regular and uniformly long. Pointed at first and becoming urn shaped as the petals unfurl. Bud opens slowly.
Color:
*When sepals first divide.*—Carmine Rose (621).
*When petals begin to unfurl.*—⅛ to ¼ inch arc of a canary yellow shade at base, shading to Nasturtium Red (14/2) and then gradually into Scarlet (19/2). This blending of colors makes an arc of about ½ inch radius, then gradually changes to Porcelain Rose (620/1) for the remaining length of the petal.
Sepals: Spear shaped. At first hooded over bud and extending about ⅛ inch beyond petals. Alternate sepals (3 of 5) are branched with lance shaped, ⅛ to ¼ inch long, marginal appendages, there being 8 to 10 on one sepal, 5 or 6 on another and 3 on one side only of the third sepal. The sepals curl back gradually and completely so by the time the flower is one-fourth open. Color: inside — near to Willow Green (000862/2) though distinctly more green in tone; outside—Lettuce Green (861/1).
Calyx: Medium size, funnel shaped and of smooth aspect. ⅝ to ¾ inch wide and ¾ to 1 inch long. Calyx does not split.
Peduncle: Very smooth and ⅜ to ½ inch long. Erect and strong but slender. Color—Lettuce Green (861/1).

*Flower*

Blooms: Profusely, with very regular production, from early spring through late fall, when outdoors. Indoors the plant blooms continuously and profusely.
Size: Medium. Diameter—3½ to 4 inches; depth—1 to 1¼ inches.
Borne: Singly and in clusters.
Shape: High center when bloom first opens, changing later, from a regular, spirally imbricate petal arrangement, to a flat cup-shaped form.
Petalage: 30 to 45 petals in very regularly imbricated arrangement.
*Form.*—Obovate, slightly serrated toward a pointed apex.
*Color.*—Outer petals—Carmine Rose (621/1) with veining of Scarlet (19/2) and having an arc, of about ¼ inch, of ivory white at petal base. Inside petals — remarkably uniform — Porcelain Rose (620/1). Reverse side—Carmine (21/2).
Petals stay on stem 5 to 6 days.
Petaloids: Number—12. Irregular—folded and crinkled inward.
*Size.*—¾ to 1 inch by 1⅛ to 1⅜ inches.
*Color.*—Same as petals.
Peduncle:
*Length.*—2½ to 2¾ inches. Sturdy and upright.
*Color.*—Lettuce Green (861/1).
Texture and appearance: Soft and satiny.
Discoloration: Very little. Fades slowly to Neyron Rose (623/2) on old flower.
Effect of weather: Bloom is lightened in color by very hot weather.
Persistence: Petals drop off cleanly.

Fragrance: Moderate musk rose.
Lasting quality:
*On plant.*—3 to 4 days.
*As cut flower.*—4 to 5 days.
Disease resistance: Resistant to mildew and somewhat resistant to rust, as observed at Livermore, California.

*Genital Organs*

Stamens:
*Anthers.*—75 to 90, irregularly arranged and ⅛ inch long.
*Filaments.*—¼ to ½ inch long. Color—Aureolin (3/1) tinged with Nasturtium Red (14).
Pollen: Color—golden yellow.
Pistils: 55 to 65. ¼ inch long.
Stigmas: Color—Sulphur Yellow (1/3) heavily tinged with anthocyanin pigment.
Ovaries: Small and crowded together.

*Fruit*

Fertility: Sterile.

As before mentioned, my new variety of rose plant most nearly resembles "Fashion" (P.P. 789) in color and "Picture" (unpatented) in flower size. My new variety differs from "Fashion," however, by having many more petals and each flower being borne on a stem long enough for cut flower use with a minimum of disbudding.

Although somewhat similar to "Seventeen" (P.P. 1,765), my new variety has more of a scarlet tone and averages larger in size.

The new variety differs from "Queen Elizabeth" (P.P. 1,259) in its color and especially the large number of petals so regularly arranged. The leaves of the new variety are more similar to "Fashion" in appearance but are larger and clothe the plant abundantly. In habit of growth my new variety is compact, like "Queen Elizabeth," but much lower-growing and more bushy when grown out-of-doors. Indoors, however, my new rose plant makes continuous vigorous growth and branches freely after cutting, breaking at 2 to 3 buds following each flower cut.

Having thus shown and described my new variety of rose plant, I claim:

A new and distinct variety of hybrid tea rose plant, substantially as herein shown and described, particularly characterized by its continuous, highly productive and regular blooming habit; by the uniform Porcelain Rose color of its high-centered, many-petaled blooms; by its vigorous habit of growth and its profuse branching, particularly after cutting for flowers; and by the large size and abundance of its foliage.

No references cited.